(12) United States Patent
Weber et al.

(10) Patent No.: US 8,187,222 B2
(45) Date of Patent: May 29, 2012

(54) DEVICES AND SYSTEMS FOR DELIVERY OF THERAPEUTIC AGENTS TO BODY LUMENS

(75) Inventors: Jan Weber, Maastricht (NL); Tracee Eidenschink, Wayzata, MN (US); Matthew Miller, Stillwater, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 174 days.

(21) Appl. No.: 12/556,756

(22) Filed: Sep. 10, 2009

(65) Prior Publication Data

US 2010/0069838 A1 Mar. 18, 2010

Related U.S. Application Data (60) Provisional application No. 61/096,496, filed on Sep. 12, 2008.

(51) Int. Cl.
*A61M 31/00* (2006.01)
*A61M 37/00* (2006.01)

(52) U.S. Cl. .................................. 604/103.02

(58) Field of Classification Search ........... 604/96.01, 604/104–109, 264, 103.01–103.14, 93.01
See application file for complete search history.

(56) References Cited

U.S. PATENT DOCUMENTS

| | | | |
|---|---|---|---|
| 4,762,130 A | 8/1988 | Fogarty et al. | |
| 5,128,197 A | 7/1992 | Kobayashi et al. | |
| 5,181,911 A | 1/1993 | Shturman | |
| 5,226,888 A | 7/1993 | Arney | |
| 5,456,667 A | 10/1995 | Ham et al. | |
| 5,484,411 A | 1/1996 | Inderbitzen et al. | |
| 5,709,874 A * | 1/1998 | Hanson et al. | 424/423 |
| 5,733,925 A | 3/1998 | Kunz et al. | |
| 6,053,900 A * | 4/2000 | Brown et al. | 604/500 |
| 6,190,356 B1 | 2/2001 | Bersin | |
| 6,280,413 B1 * | 8/2001 | Clark et al. | 604/104 |
| 6,280,414 B1 * | 8/2001 | Shah et al. | 604/104 |
| 6,524,274 B1 * | 2/2003 | Rosenthal et al. | 604/96.01 |
| 6,540,849 B2 | 4/2003 | DiCarlo et al. | |
| 7,364,585 B2 | 4/2008 | Weber | |
| 2002/0103446 A1 | 8/2002 | McFann et al. | |

(Continued)

FOREIGN PATENT DOCUMENTS

WO 00/48645 A2 8/2000

(Continued)

OTHER PUBLICATIONS

"Biodegradable Shape-Memory Polymers Developed", European Medical Device Manufacturer, Sep. 2002, p. 1; http://www.devicelink.com/emdm/archive/02/09/012.html, downloaded May 31, 2006.

(Continued)

*Primary Examiner* — Christopher D Koharski
(74) *Attorney, Agent, or Firm* — Mayer & Williams PC; David B. Bonham; Keum J. Park (57) ABSTRACT

In accordance with one aspect, the invention provides medical devices that comprise an elongated drug delivery member, which is adapted to take on a radially expanded configuration upon actuation in vivo.

18 Claims, 4 Drawing Sheets

U.S. PATENT DOCUMENTS

| | | |
|---|---|---|
| 2002/0193735 A1 | 12/2002 | Stiger |
| 2003/0055198 A1 | 3/2003 | Langer et al. |
| 2004/0015151 A1* | 1/2004 | Chambers .................... 604/532 |
| 2004/0093076 A1 | 5/2004 | White et al. |
| 2004/0167509 A1 | 8/2004 | Taimisto |
| 2005/0177130 A1 | 8/2005 | Konstantino et al. |
| 2006/0217653 A1 | 9/2006 | Doty |
| 2007/0088244 A1 | 4/2007 | Miller et al. |
| 2007/0123839 A1 | 5/2007 | Rousseau et al. |
| 2008/0015541 A1 | 1/2008 | Rosenbluth et al. |
| 2008/0085294 A1 | 4/2008 | Freyman et al. |

FOREIGN PATENT DOCUMENTS

| | | |
|---|---|---|
| WO | 00/66199 A1 | 11/2000 |
| WO | 00/72907 A1 | 12/2000 |
| WO | 2004/098697 A1 | 11/2004 |
| WO | 2006/109945 A1 | 10/2006 |

OTHER PUBLICATIONS

B. Scheller et al., "Addition of Paclitaxel to Contrast Media Prevents Restenosis After Coronary Stent Implantation" Journal of the American College of Cardiology, vol. 42, No. 8, (2003), pp. 1415-1420.

A. Lendlein et al., "Light-induced shape-memory polymers", Nature, vol. 434, Apr. 14, 2005, pp. 879-882.

A. Lendlein et al., "Shape-Memory Effect", Angew. Chem. Int. Ed., (2002), vol. 41, pp. 2034-2057.

D. Needham et al., "The development and testing of a new temperature-sensitive drug delivery system for the treatment of solid tumors", Advanced Drug Delivery Reviews, vol. 53 (2001), pp. 285-305.

U.S. Department of Health and Human Services, AHRQ Technology Assessment Program, "Vulnerable Plaques: A Brief Review of the Concept and Proposed Approaches to Diagnosis and Treatment", Jan. 22, 2004, pp. 11-16.

* cited by examiner

DEVICES AND SYSTEMS FOR DELIVERY OF THERAPEUTIC AGENTS TO BODY LUMENS

RELATED APPLICATIONS

This application claims priority from U.S. provisional application 61/096,496, filed Sep. 12, 2008, which is incorporated by reference herein in its entirety.

FIELD OF THE INVENTION

The present invention is directed to medical devices for delivery of therapeutic agents to body lumens.

BACKGROUND OF THE INVENTION

The in-situ delivery of therapeutic agents within the body of a patient is common in the practice of modern medicine. In-situ delivery of therapeutic agents is often implemented using medical devices that may be temporarily or permanently placed at a target site within the body. These medical devices can be maintained, as required, at their target sites for short or prolonged periods of time, in order to deliver therapeutic agents to the target site.

For example, in recent years, drug eluting coronary stents, which are commercially available from Boston Scientific Corp. (TAXUS, PROMUS), Johnson & Johnson (CYPHER) and others, have been widely used for maintaining vessel patency after balloon angioplasty. These products are based on metallic expandable stents with polymer coatings that release anti-restenotic drugs at a controlled rate and total dose.

Therapeutic agents have also been delivered to vessel walls using balloons. For example, there have been clinical trials showing that in-stent restenosis can be treated using a balloon having a sprayed coating of pure paclitaxel.

Although a paclitaxel coated balloon has been shown efficient in trials, it may not always be the most desirable treatment scheme for a variety of reasons. For example, delivery of a consistent amount of drug to the lesion site may be an issue due to drug loss during delivery to the lesion (and vessel wall) before and after balloon inflation. Moreover, the contact time between the therapeutic-agent-coated surface and the vessel wall maybe limited due to the fact that the balloon acts to block blood flow. Furthermore, dilatation of a vessel by means of some balloons may cause overstretching of tissues in the vessel wall, which can result in recoil or stress induced inflammatory effects. For these effects one can place a stent in the vessel to prevent recoil as well as to provide a drug coating to prevent short term inflammatory reactions.

SUMMARY OF THE INVENTION

The present invention provides alternatives to balloons for the non-stent delivery of drugs to body lumens.

In accordance with one aspect, the invention provides medical devices that comprise an elongated drug delivery member, which is adapted to take on a radially expanded configuration upon actuation in vivo.

The above and other aspects, as well as various embodiments and advantages of the present invention, will become readily apparent to those of ordinary skill in the art upon review of the Detailed Description and any claims to follow.

DETAILED DESCRIPTION OF THE INVENTION

"Therapeutic agents", "pharmaceuticals," "pharmaceutically active agents", "drugs" and other related terms may be used interchangeably herein.

As previously noted, the present invention provides alternatives to balloons for the non-stent delivery of drugs to body lumens.

In accordance with one aspect, the invention provides medical devices that comprise an elongated drug delivery member, which is configured to adopt a radially expanded configuration upon actuation in vivo. As will be seen from the description to follow, actuation mechanisms include radial expansion due to mechanical actuation, radial expansion due to elastic rebound, radial expansion due to thermal effects (e.g., heating due to electrical current, heating using heated fluid, etc.) and radial expansion due to illumination.

Examples of elongated drug delivery members include elongated structures of solid cross-section (e.g., wires, rods, filaments, strands, strips, ribbons, etc.) and elongated structures of hollow cross-section (e.g., single-lumen structures such as tubes, multi-lumen structures, etc.).

Elongated drug delivery members in accordance with the invention may take on a number of configurations. For example, in various embodiments, elongated drug delivery members in accordance with the invention are configured such that when the longitudinal distance between the proximal and distal ends of the elongated member is reduced (i.e., longitudinal contraction) the elongated member undergoes a radial expansion. Examples of such structures include simple arcs, helices, and, in general, all shapes that follow a curve around the central longitudinal axis for which a compression along the longitudinal axis results is an expansion in radial dimension of the curved shape. In terms of actuation, in some embodiments, the distal end of the drug delivery member may be longitudinally retracted mechanically with within a body lumen such as a blood vessel while keeping proximal end fixed, the proximal end of the delivery member may be longitudinally advanced mechanically with within a body lumen while keeping distal end fixed, or the proximal end of the delivery member may be longitudinally advanced simultaneously with retraction of the distal end. In other embodiments, longitudinal contraction and radial expansion occur as a result of a shape memory effect.

Figure 1A:
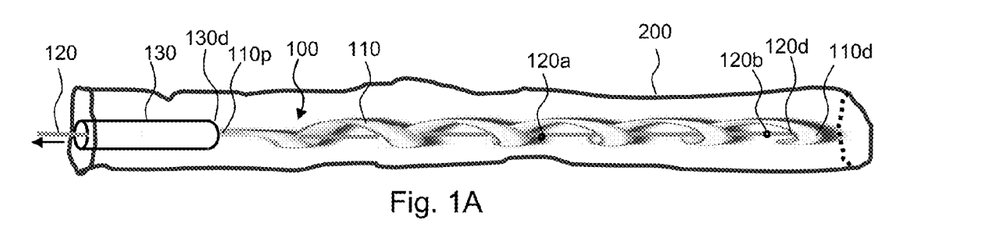
FIG. 1A is a partial schematic illustration of a drug delivery device in accordance with an embodiment of the invention, disposed within a body lumen.
Figure 1B:
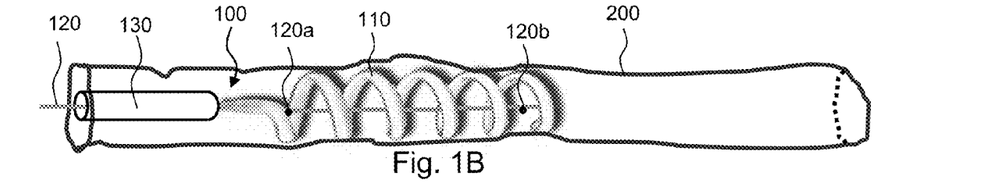
FIG. 1B is a schematic illustration of the drug delivery device of FIG. 1A, subsequent to actuation and radial expansion.

A few exemplary embodiments of the invention will now be described with reference to the drawings. FIG. 1A is a partial schematic illustration of a drug delivery device 100 in accordance with an embodiment of the invention, disposed within a blood vessel 200. The drug delivery device 100 includes a helical elongated drug delivery member 110 having a distal end 110d and a proximal end 110p. The proximal end 110p of the helical elongated member 110 is attached to the distal end 130d of a tubular member 130. The tubular member 130 extends proximally through the vasculature such that the proximal end of the tubular member 130 (not shown) is external to the body of the patient. The drug delivery device 100 further includes an elongated actuation member 120, whose distal end 120d is attached to the distal end 110d of the helical elongated member 110. As with certain other embodiments herein, a first additional elongated member (e.g., a tubular member 130) is connected at or near one end of the elongated drug delivery member 110 and a second additional elongated member (e.g., an actuation member 120) is connected at or near the opposing end of the elongated drug delivery member. Also shown in FIG. 1A are reference points 120a and 120b along the length of the elongated actuation member 120. In the embodiment shown, the drug delivery member 110 is configured such that when the longitudinal distance between the proximal and distal ends of the elongated member is reduced (i.e., longitudinal contraction) the drug delivery member 110 undergoes radial expansion. More particularly, in the embodiment shown, the drug delivery member 110 is radially expanded by retracting the elongated actuation member 120 (e.g., a pull wire) relative to the tubular member 130 by pulling the elongated actuation member 120 in the direction of the arrow in FIG. 1A. Referring now to FIG. 1B, this retraction of the elongated actuation member 120 results in a longitudinal shortening of the drug delivery member 110, which is accompanied by a radial expansion such that the outer surface of the helical drug delivery member 110 comes into contact with the blood vessel 200. Movement of the elongated actuation member 120, which is attached only to the distal end 110d of the helical elongated member 110 and is unattached to the tubular member 130, relative to the other components can perhaps be better seen by reference to the reference points 120a and 120b along the length of the elongated actuation member 120. After the blood vessel has been exposed to the helical elongated drug delivery member 110 for a desired period of time, the device can be radially contracted by advancing the elongated actuation member 120 to its original, radially contracted, position. If desired, the drug delivery device 100 of FIGS. 1A and 1B can be advanced into the vasculature through larger tubular member (not shown) or may be provided within a retractable sheath (not shown). If desired, marker bands (not shown) may be provided to monitor the position of the ends of the helix before, during and after expansion.

In an alternative to the construction of the device of FIGS. 1A and 1B, a drug delivery member 110 is employed that changes in bending stiffness along its length such that the helix engages the vessel wall beginning with the least stiff section and ending with the most stiff section.

Figure 2A:
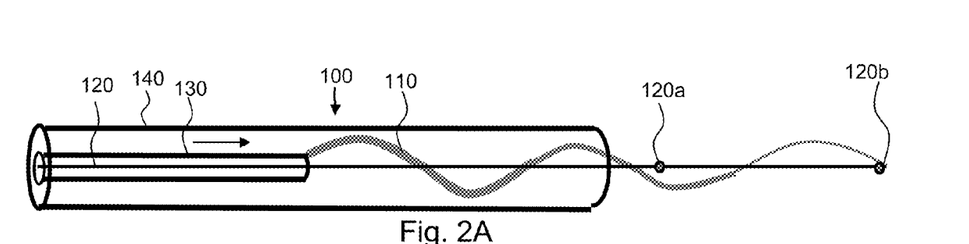
FIGS. 2A-2C are partial schematic illustrations of a drug delivery device in accordance with an embodiment of the invention, at various stages of actuation and radial expansion.
Figure 2B:
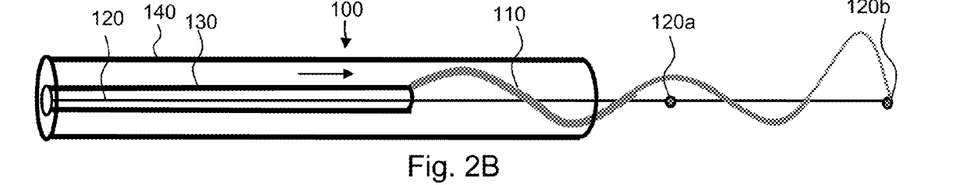
Figure 2C:
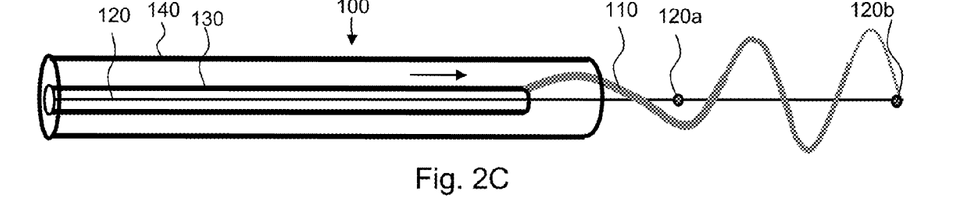

This effect can be seen, for example, with reference to FIGS. 2A-2C. FIG. 2A is a schematic illustration of a drug delivery device 100 in accordance with an embodiment of the invention. Like FIG. 1A, the device 100 of FIG. 2A includes a helical elongated drug delivery member 110, the proximal end of which is attached to the distal end a tubular member 130 and the distal end of which is connected to the distal end of an elongated actuation member 120. Also shown in FIG. 2A are reference points 120a and 120b along the length of the elongated actuation member 120. Unlike FIG. 1A, the device 100 of FIG. 2A includes a larger tubular member 140 (e.g., to retain drug on the drug delivery member prior to its expulsion from the tubular member 140). Moreover the thickness and thus the stiffness of the helical elongated drug delivery member 110 (whose at rest shape is shown in FIG. 2A) decreases as one proceeds from the proximal end to the distal end of the member 100. During actuation, the tubular member 130 (which may be formed from a stiff material such as a metal or a stiff polymer) is pushed forward relative to the elongated actuation member 120 (and the tubular member 140 as well), thereby reducing the longitudinal length of the helical member 110 and forcing the helical member 110 to expand radially. Because the helical member 110 is least stiff at its distal end, the distal end expands to touch the vessel wall first, with the expansion of further portions of the helical member 110 moving in the proximal direction as shown in FIGS. 2B and 2C.

In the construction of the device of FIGS. 1A and 1B, the length of the helical drug delivery member 110 changes when the pull wire 120 is pulled back. In other embodiments, the length of the member 110 remains relatively constant during device deployment. For example, the helical member 110 of the device 100 of FIG. 1A may be radially expanded by rotating the tubular member 130 clockwise (when viewed from the proximal end) relative to the elongated actuation member 120. In this instance, the radial expansion is accompanied by a reduction in the number of windings within the helical member 120. Conversely the device 100 may be radially contracted by rotating the tubular member 130 counterclockwise relative to the elongated actuation member 120, which contraction is accompanied by an increase in the number of windings within the helical member 120.

In other embodiments, an elastic sleeve (not shown) may be provided over the helix, with a lubricant provided between the helical member and the sleeve. The sleeve may be, for example, a soft polymeric sleeve, such as a soft durometer polyurethane (e.g., Tecothane). The sleeve may also be loaded with a therapeutic agent, for instance supplied within holes that are formed in the sleeve material, distributed throughout the sleeve material (which material acts as a matrix for the therapeutic agent) and so forth. Such a sleeve may be advantageous in that the total length of the delivery region stays fixed. Such a sleeve may also be advantageous for therapeutic agent delivery in that it provides increased contact area with the blood vessel. A sleeve of this type may be used in any of the various other embodiments described herein.

The above discussion notes that the device 100 of FIGS. 1A and 1B may be radially expanded by longitudinally retracting the elongated actuation member 120 while maintaining the longitudinal position of the tubular member 130. Moreover, the device 100 could also be actuated by actuated by longitudinally advancing the tubular member 130 while maintaining the longitudinal position the elongated actuation member 120. Similarly, while the above discussion indicates that the device 100 may be radially contracted by longitudinally advancing the elongated actuation member 120 while maintaining the longitudinal position of the tubular member 130, the device 100 could also be radially contracted by longitudinally retracting the tubular member 130 while maintaining the longitudinal position the elongated actuation member 120.

Note that while a single helical member 110 is shown in FIGS. 1A and 2A, multiple helical members may be provided (a) all of which may rotate in the same direction around the central longitudinal axis of the device or (b) one or more of which may rotate in a first direction around the central longitudinal axis of the device and one or more of which may rotate in a second direction around the central longitudinal axis of the device that is opposite that of the first direction.

Figure 3:
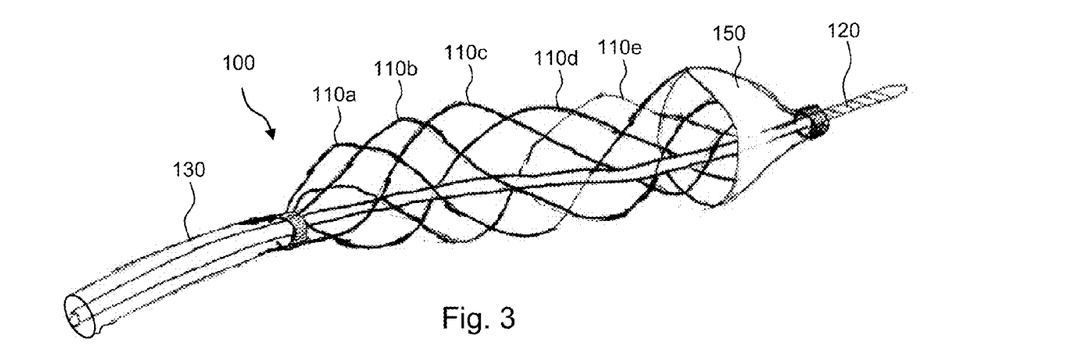
FIG. 3 is a partial schematic illustration of a drug delivery device in accordance with an embodiment of the invention.

For example, FIG. 3 is a schematic illustration of a drug delivery device 100 in accordance with an embodiment of the invention. The catheter 100 of FIG. 3 includes five helical elongated drug delivery members 110a-110e (five are shown, but 2, 3, 4, 6, 7, 8, 9, 10 or more members may be employed), the proximal ends of which are coupled to the distal end a tubular member 130 and the distal ends of which are coupled to the distal end of an elongated actuation member 120. The device 100 of FIG. 3 further includes a distal protection filter 150, which may comprise, for example, 20 micron holes to allow for blood flow while at the same time capturing any debris that may be generated by the device. As with the preceding devices, the helical members may be radially expanded by reducing the longitudinal length of the helices or by rotating the tubular member 130 clockwise (when viewed from the proximal end) relative to the elongated actuation member 120.

Figure 4A:
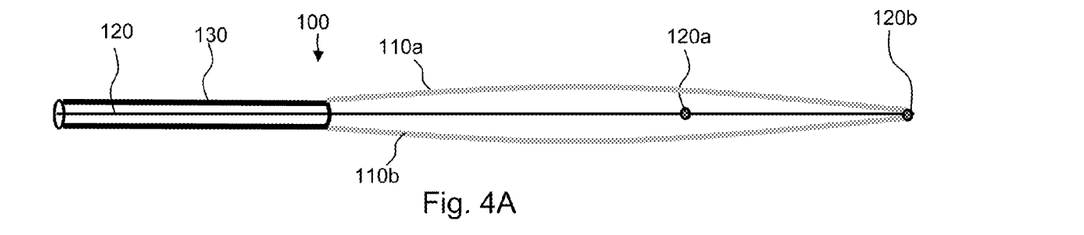
FIGS. 4A-4B are partial schematic illustrations of a drug delivery device in accordance with an embodiment of the invention, at two stages of actuation and radial expansion.
Figure 4B:
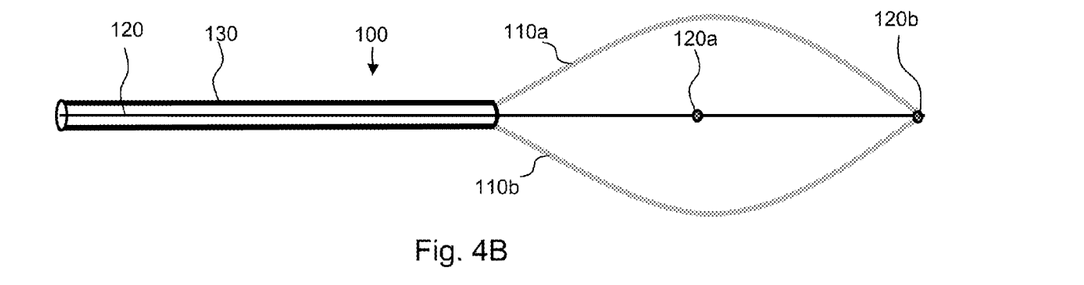

In the preceding embodiments, the elongated drug delivery members employed are helical members, although elongated drug delivery members having other shapes, including other curvilinear shapes may be employed. FIG. 4A is a schematic illustration of a drug delivery device 100 that includes a plurality of arc-shaped elongated drug delivery members 110a-110b (two are shown, but 3, 4, 5, 6, 7, 8, 9, 10 or more members may be employed), the proximal ends of which are coupled to the distal end of an elongated tubular member 130 and the distal ends of which are coupled to the distal end of an elongated actuation member 120. In the embodiment shown, the member 110 undergoes radial expansion when the longitudinal distance between the proximal and distal ends of the elongated member is reduced (i.e., longitudinal contraction), for example, by advancing the tubular member 130 while holding the elongated actuation member 120 fixed or by withdrawing the elongated actuation member 120 while holding the tubular member 130 fixed. The result of this action is shown in FIG. 4B.

In the preceding embodiments, drug delivery members are employed which are actuated mechanically by the user (e.g., a health care practitioner), in particular, by means of an elongated actuation member such as a pull wire or a push rod that is external to the drug delivery member.

In other embodiments, the elongated actuation member is internal to the drug delivery member. For example, referring now to FIG. 5A, a drug delivery device 100 is shown which includes a drug delivery member 110. Disposed on the surface of the drug delivery member 110 is a therapeutic-agent containing region 218. The drug delivery member 110 is formed of a polymer material such as Polyamide 12, silicon rubber or polyurethane and contains two off-center lumens, one of which contains a wire 125 that is fixed along its length to the drug delivery member 110 and the other of which contains a wire 120 that is slidable within the drug delivery member 110 lumen, except for the fact that it is fixed to the distal end of the drug delivery member 110. The proximal end of the drug delivery member 110 may itself be fixed to the distal end of a stiff elongated tubular member (not shown), through which the wire 120 extends back to the proximal end of the catheter system.

Figure 5A:
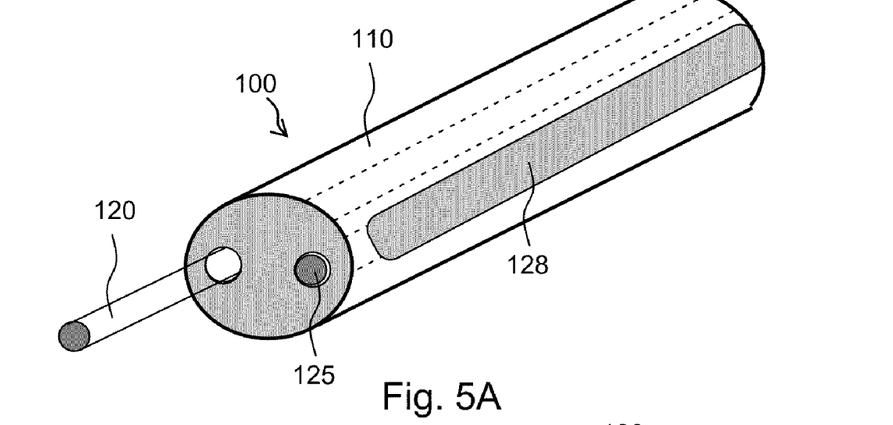
FIG. 5A is a partial schematic illustration of a drug delivery device in accordance with an embodiment of the invention.
Figure 5B:
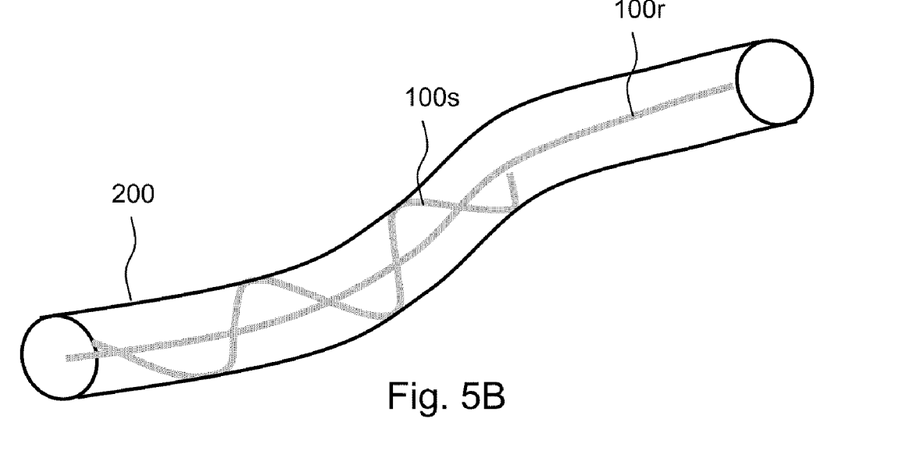
FIG. 5B is a partial schematic illustration of the drug delivery device of FIG. 5A, disposed within a body lumen, at two stages of actuation and radial expansion.

The mode of operation of the device of FIG. 5A is very simple. Specifically, as shown in FIG. 5B, the elongated drug delivery member is initially in a relaxed relatively linear state 100r upon introduction into a body lumen 200. By pulling the wire 120 with respect to the drug delivery member 110, however, the drug delivery member 110 is forced to bend into a spiral shape 110s, forcing the drug delivery member 110 against the body lumen wall 200 in a position where the side of the drug delivery member 110 that contains the fixed wire 125 (and the drug-containing region 218) faces the lumen wall 200. The slidable wire 120 can be tensioned on the hub end of the stiff elongated tubular member by a screw system. Releasing the slidable wire 120 will allow the drug delivery member 110 to straighten back into a relaxed relatively linear state 100r, allowing it to be withdrawn from the patient.

In an alternative embodiment to that of FIG. 5A, only a single offset lumen with the slidable wire 120 is employed (i.e., the other lumen with the fixed wire 125 is not included).

Figure 6:
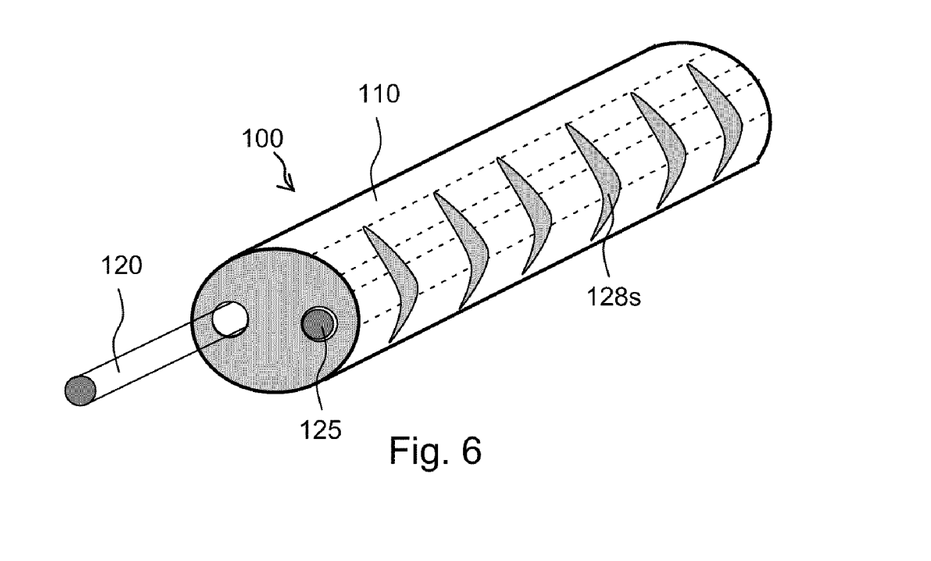
FIG. 6 is a partial schematic illustration of a drug delivery device in accordance with an embodiment of the invention.

In the device of FIG. 5A, the drug-containing region is a drug containing layer. In other embodiments, the drug delivery member 110 will be provided with a series of drug-filled slits 128s as shown in FIG. 6. Analogous to bending a cracked rubber rod, these slits will open up when the tube is forced into a helical shape inside the blood vessel by pulling the wire 120. The slits may also aid in the formation of a helical shape with the correct orientation (i.e., an orientation where the drug-filled slits 128s facing the vessel wall), due to differences in bending stiffness on the slitted side of the drug delivery member versus the non-slitted side.

Another option is to provide the surface of the drug delivery member 110 with pressure-sensitive, drug-loaded capsules, for example, such as those described in U.S. Pat. No. 7,364,585 to Weber.

In other embodiments, drug delivery members are delivered in conjunction with an elongated tubular member (e.g., a tubular delivery catheter) that initially holds the member in a radially confined state. The elongated tubular member and the drug delivery member are advanced into the patient at which point the elongated tubular member is retracted relative to the drug delivery member (or the drug delivery member is advanced relative to the elongated tubular member). Upon emerging from the elongated tubular member, the drug delivery member expands due to elastic rebound, engaging the vessel wall.

Figure 7A:
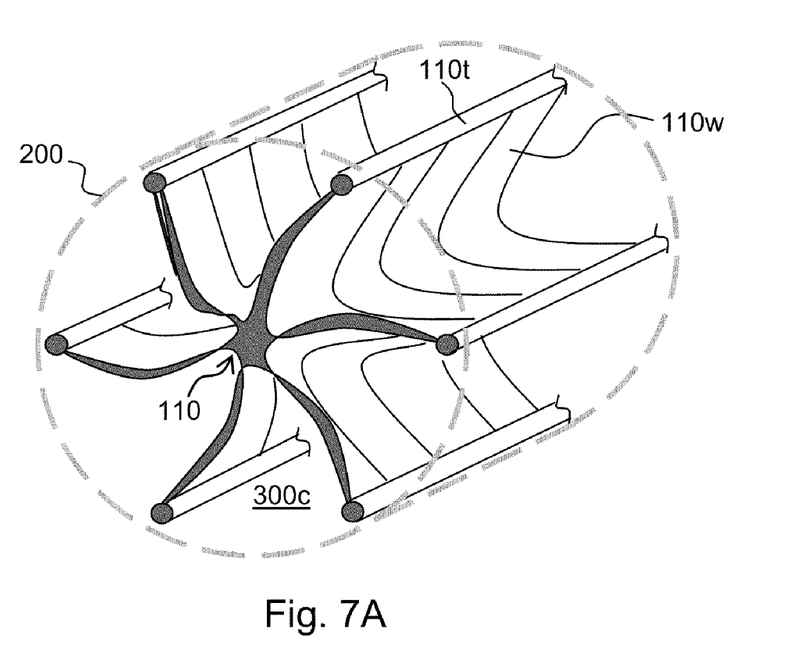
FIG. 7A is a partial schematic illustration of a drug delivery device in accordance with an embodiment of the invention.

One embodiment of a drug delivery member 110 of this type is illustrated in the partial cross-sectional view of FIG. 7A. The drug delivery member 110 has a star-shaped cross-section and is formed from a soft material which is able to elastically rebound from a compressed/folded configuration (e.g., silicone rubber, etc.) into an expanded configuration that contacts the vessel wall 200 (designated by dashed lines). The drug delivery member 110 shown has six wings 110w, however another number of wings may be employed (e.g., two, three, four, five, seven, eight or more). The member shown has slightly curved wings 110w such that the wings preferentially fold in one direction (clockwise in the view shown). At the end of each wing 110w in the embodiment shown, there is a thicker section 110t that is loaded with the drug and thus acts as a depot for the drug. If desired, the wing surfaces may be textured (e.g., by embossing, etc.), allowing drug containing compositions to be loaded into depressions, such as dimples, grooves, slits etc.

Figure 7B:
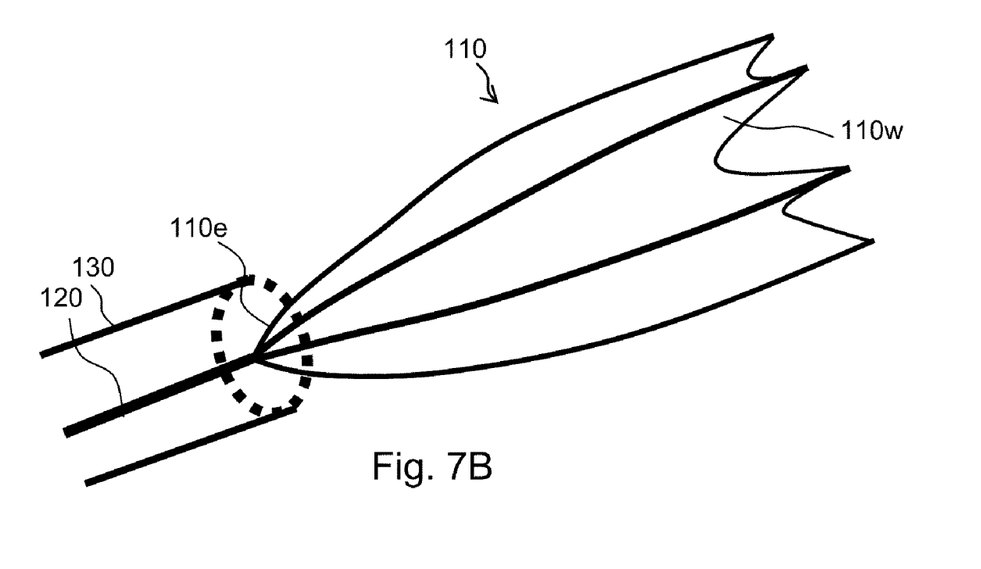
FIG. 7B is a partial schematic illustration of the tapered end of a drug delivery device like that of FIG. 7A adjacent an associated delivery catheter.

In certain embodiments such as that shown in FIG. 7B, the proximal end 110e of the drug delivery member 110 is tapered to assist refolding when the drug delivery member 110 is pulled back into the elongated tubular member 130 via push/pull wire 120.

In addition to (or as an alternative to) providing drug on or in the drug delivery member 110, for instance by using all or a part (e.g., regions 110*t*) of the drug delivery member itself as a drug-containing matrix, by providing one or more drug containing regions on or in the drug delivery member, and so forth, in other embodiments, a drug is provided by injecting a drug containing fluid into one (or more) of the channels 300*c* (six shown) as created between the vessel wall 200 and the member 110. The other channels can used to provide blood flow.

One very specific application of such a device is in the treatment of vulnerable plaques, in which the disease is on one side of the vessel. In this case, the member 110 may be expanded in the blood vessel 200, after which by means of a suitable detection device (e.g., an optical fiber, a thermo-element, etc.) one may detect which of the channels is oriented towards the diseased area. One may then advance a catheter down the detected channel and inject drug in the diseased area. For instance, one may advance a small catheter tube with a soft, very compliant balloon (e.g., a silicone balloon) on its end into the channel, which balloon could be inflated to close off the distal end of the channel. Once the channel is closed on the distal end, one may inject the drug-containing fluid into the space that is formed (e.g., via a side-hole in the catheter), thereby treating the diseased area.

In other embodiments, a device like that shown in FIG. 7A may be provided, except that the cross sectional shape is rotated as one advances along the axis of the device, providing a drug delivery member with a screw-like appearance. Such embodiments may provide enhanced flexibility when advanced through tortuous vessels.

Various devices described herein, including the devices of the various Figures, may be used for the delivery of multiple drugs. For example, the devices may be used to deliver a mixture of two or more drugs to the wall of a body lumen. For instance, in the treatment of plaque, one, two or more drugs selected from the following may be released: anti-inflammatory agents including metalloprotease inhibitors, sclerotic agents (to stabilize the thin cap fibrous atheroma of vulnerable atherosclerotic plaque), lipid-lowering drugs, including statins, ACE inhibitors, beta blockers, antioxidants, macrolide antibiotics, and antithrombotic agents such as aspirin, among others. See, e.g., Pub. No. US 2008/0085294 to Freyman et al. and U.S. Dept. of Health and Human Services, AHRQ, "Vulnerable Plaques: A Brief Review of the Concept and Proposed Approaches to Diagnosis and Treatment," Jan. 22, 2004, pp. 11-16.

Various devices of the present invention may also be used to deliver one or more drugs to wall of a body lumen and one or more different drugs to the fluid within the body lumen. For instance, in the case of a blood vessel, one or more drugs for the treatment of plaque may be released from the surface(s) of the drug delivery member(s) that contact(s) the blood vessel wall and one or more anti-thrombotic drugs may be relapsed from the surface(s) of the drug delivery member(s) that contact(s) the blood. For example, such drugs may be provided within distinct portions of the drug delivery member(s) that act as drug-containing matrices, within drug releasing coatings on the drug delivery member(s), or within drug releasing compositions disposed within depressions formed in the drug delivery member(s), among other possibilities.

As seen from the above described examples, in many embodiments, the drug delivery members of the invention are adapted to be removed after deployment, typically by placing the device in a radially contracted state which allows for removal. Also, the devices of the invention are permanently attached to one or more elongated delivery members (e.g., a tube, rod, etc.) in many embodiments. In this sense, such devices are fundamentally different from stents and other implantable devices, which are adapted to remain in the body after deployment.

As previously indicated, one advantage of the devices of the present invention relative to balloons is that the devices do not completely block blood flow. Consequently, the contact time between the devices and the vessel wall can be quite long. For example, in many embodiments, the elongated members have a total cross-sectional area (e.g., $n\pi r^2$ for n members of circular cross section where r is the radius) that is substantially smaller than the blood vessel through which it is adapted to be advanced, typically less than 50%, and preferably less than 25% of the cross sectional area of the body lumen to be treated.

Another advantage of the devices of the present invention relative to balloons is that the devices can be used to treat relatively long stretches of tissue. For example, in the treatment of blood vessels, including blood vessels in the legs, the devices may be configured such that, when in an expanded configuration, the devices make contact with the blood vessel over a distance ranging from 1 cm to 20 cm or more.

The materials used to form elongated tubular members and elongated actuation members such as those described above vary widely, with the ultimate selection depending, for example, upon whether such members are placed into tension (which will require a degree of tensile strength and inelasticity) or compression (which will require a degree of column strength and incompressibility). Typical materials for these elements include metals and relatively rigid plastics.

The materials used to form the elongated drug delivery members of the invention also vary widely. For example, in certain embodiments, the members are formed from relatively stiff materials. Examples of such materials include stiff polymers (e.g., polycarbonates, high density polyethylene, etc.) and metals (e.g., superelastic metals such as alloys that comprise nickel and titanium, particularly, nitinol, spring-steel, alloys comprising nickel, cobalt and chromium, such as MP 35N, etc.)

In other embodiments, the members are formed from a relatively soft and flexible material that is able to adapt to the geometry of the body lumen into which it is inserted, including vascular side branches and other side vacancies (e.g., aneurysms, bronchial branches, etc.) of body lumens. Examples of such materials include polymers which are flexible, but which also have sufficient rigidity to expand outwardly, for example, due to mechanical actuation or due to elastic rebound (e.g., silicone, polyurethanes, etc.).

In certain embodiments, the geometry of the elongated drug delivery member is selected to achieve enhanced adaptability to body lumens. For example, a member may be provided which has an overall primarily helical shape but which has a secondary sinusoidal or zig-zag shape superimposed on the helical shape as one travels along the length of the member.

Methods of forming the elongated drug delivery members of the invention include molding techniques in which the members are formed in an original configuration which, as discussed elsewhere herein, may be modified by exerting a force upon the material or which may be trained to return to its original form upon application of energy, for example, heat or light (e.g., shape memory materials).

Where the delivery members of the invention are modified by exerting a mechanical force upon the material, the delivery member may be molded in a form that is radially compressed when no force is exerted upon the member (which form is expanded by the application of force and contracted by the removal of force). Alternatively, the elongated member may be molded in a form that is radially expanded when no force is exerted on the member (which form is contracted by the application of force and expanded by the removal of force).

Further materials for the delivery members include shape memory materials that expand upon application of heat or light. Heat may be applied, for example, by the passage of electrical current through the shape memory material (e.g., where conductive), by the passage of heated fluid through the material (e.g., where a tubular shape memory material is employed), and by shining light, particularly infrared light, on the material. Light may be applied using, for example, an optical fiber, in which case different portions of the shape memory material may be expanded at different times (e.g., from the distal end to the proximal end, from the proximal end to the distal end, etc.) by moving the optical fiber along the length of the material. Alternatively, the material may be illuminated (and thus expand) all at once.

Materials, including shape memory alloys and polymers, are said to show a shape memory effect if they can be deformed and fixed into a temporary shape, and subsequently approach or completely return to their original (or "permanent") shape upon exposure to an activating stimulus.

As is known, shape memory materials are stimuli-responsive materials that have the capability of changing their shape upon application of an external stimulus, such as thermal, electrical, solvent, pH, pressure, or light stimulus, or any other suitable stimulus. A change in shape caused by a change in temperature is called a thermally induced shape memory effect. Such materials include one-way shape memory materials, which "remember" only the permanent shape, and two-way materials, which are capable of remembering two shapes. One-way shape materials may be retrieved after expansion in a body lumen, for example, by withdrawing them into an elongated tubular member, followed by removal of the elongated tubular member from the patient.

In the present invention, thermally activated shape memory materials may be selected for which a shape change in the material occurs at temperatures somewhat greater than normal body temperature (e.g., ranging from 38 to 40 to 42 to 44 to 46 to 48 to 50° C. or more).

Of the various shape memory metals and alloys, those nickel-titanium alloys known as nitinol are perhaps the best known. Nitinol shape memory alloys can exist in a two different temperature-dependent crystal structures (phases) called martensite (lower temperature phase) and austenite (higher temperature or parent/permanent phase). When martensite nitinol is heated, it begins to change into austenite. The temperature at which this phenomenon starts is called austenite start temperature ($A_s$). The temperature at which this phenomenon is complete is called austenite finish temperature ($A_f$). On the other hand, when austenite Nitinol is cooled, it begins to change onto martensite. The temperature at which this phenomenon starts is called martensite start temperature ($M_s$). The temperature at which martensite is completely reverted is called martensite finish temperature ($M_f$). Composition and metallurgical treatments can impact these temperatures.

Nitinol is well known for its shape memory and superelastic (or pseudoelastic) properties. When the material is in its martensite form, it is soft and ductile and can be easily deformed, while superelastic Nitinol is highly elastic (rubber-like). Austenitic Nitinol, on the other hand, is quite strong and hard (similar to titanium). The Nitinol material has all of these properties, with the specific expression depending on the temperature environment in which it is used.

Generally, the shape memory effect allows the alloy to be (a) provided in a first shape while in the relative high-temperature austenite phase, (b) cooled below a transition temperature range, for example, from $M_s$ down to $M_f$ or below, whereupon the austenite is partially (between $M_s$ and $M_f$) to completely (at $M_f$ or below) transformed into the relative low-temperature martensite phase, (c) deformed while in a martensite phase into a second configuration, and (d) heated back to the austenite transition temperature range, specifically from $A_s$ up to $A_f$ or above, such that the alloy transforms partially (between $A_s$ and $A_f$) to completely (at $A_f$ or above) from the second configuration back to the first configuration. This is called one-way shape memory.

Superelasticity refers to the ability of Nitinol to return to its original shape upon unloading after a substantial deformation. This is based on stress-induced martensite formation. The application of an outer stress to an austenite sample causes martensite to form at temperatures higher than $M_s$. The macroscopic deformation is accommodated by the formation of martensite. When the stress is released, the martensite transforms back into austenite and the specimen returns back to its original shape. The highest temperature at which martensite can no longer stress induced is called $M_d$. Superelasticity typically appears in a temperature range from near $A_f$ and up to $M_d$. Nitinol in this temperature range is thus suitable for applications requiring recoverable deformation. For example, conventional pseudoelastic Nitinol is useful for applications requiring recoverable strains of up to 8% or more. For further information, see, e.g., U.S. Pat. No. 6,540,849 to DiCarlo et al., and the references cited therein.

With shape memory polymers, the process of programming and recovery of a shape is generally as follows: (a) first, the polymer is conventionally processed to receive its original, or permanent, shape, (b) the polymer is then deformed and the intended temporary shape is fixed in a process called programming, which typically consists of heating the sample above a transition temperature, deforming it, and cooling it below the transition temperature while in the deformed state. The permanent shape is now stored while the sample shows the temporary shape. Subsequent heating of the shape memory polymer above the transition temperature leads to the recovery of the stored, permanent shape. Typically, upon cooling of the polymer, no recovery of the temporary shape is observed. This effect is known as a one-way shape memory effect. Dimensional changes within shape memory polymers may be on the order of, for example, 100-1000%. For example, segmented polyurethanes developed by Mitsubishi Heavy Industries in Nagoya, Japan are reported to have dimensional changes of about 200%. As another example, "Biodegradable Shape-Memory Polymer Developed," *European Medical Device Manufacturer*, September 2002 describes a biodegradable polymer developed by Andreas Lendlein and Robert Langer, which can achieve recoverable deformations of up to 1000% in some cases.

Specific examples of shape memory polymers include block copolymers and covalently linked polymer networks. These polymers may exhibit a shape memory functionality by using the polymer chains as a type of molecular switch. One possibility for a switch function is a thermal transition of the chains in the temperature range of interest for a particular application (e.g., between room and body temperature, etc.). At temperatures above the thermal transition temperature ($T_{trans}$) the chain segments become more flexible, whereas the flexibility of the chains below this thermal transition is at least partly limited.

Phase-segregated multiblock copolymers, commonly linear block copolymers, are known to display at least two separated phases. The phase showing the highest thermal transition $T_{perm}$ (sometimes referred to as the hard phase) provides physical cross-links (also referred to sometimes as "physical netpoints") and is responsible for the permanent shape of the material. (Above this temperature the polymer commonly melts and can be processed by conventional processing techniques such as extrusion, injection molding, melt spinning, etc.) The portion of the block copolymer that forms the hard phase is sometimes referred to as the hard segment. A second phase (i.e., a switching phase) enables the fixation of the temporary shape. The portion of the block copolymer that forms the switching phase is sometimes referred to as the switching segment. The transition temperature ($T_{trans}$) for the fixation of the switching phase is typically either a glass transition temperature ($T_g$) or a melting temperature ($T_m$). In the case of a melting temperature, one observes a relatively sharp transition in most cases, whereas glass transitions typically extend over a broader temperature range. After applying a force that is sufficient to deform the material at a temperature above $T_{trans}$ but below $T_{perm}$, a temporary shape is achieved, which can be fixed by cooling the polymer below $T_{trans}$ while continuing to apply the deformation force. The deformation force may then be removed. Subsequent heating of the material above $T_{trans}$ returns the material to its permanent shape.

Specific examples of known multiblock copolymers with $T_{trans}=T_{melt}$ include (a) multiblock copolymers of polyurethanes with poly($\epsilon$-caprolactone) switching phases, for example, polyesterurethanes such as those with a hard phase segment based on methylenebis(4-phenylisocyanate) (MDI) and 1,4-butanediol, and with a switching phase segment based on poly($\epsilon$-caprolactone) having a number-average molecular weigh ($M_n$) between 1600 and 8000, for which the switching temperature for the shape memory effect may vary, for example, between 44 and 55° C., depending on the weight fraction of the switching segments and the molecular weight of the switching segments, (b) block copolymers with a hard phase segment based on polyethylene terephthalate (PET) and switching phase segment based on polyethylene oxide (PEO), for which the thermally induced shape memory effect is triggered by the melting temperature of the PEO crystallites and may vary, for example, between 40 and 60° C. depending on the molecular mass of the PEO blocks and on the PET content, (c) block copolymers with a hard phase segment based on polystyrene and switching phase segment based on poly(1,4-butadiene), for which the thermally induced shape memory effect is triggered by the melting temperature of the poly(1,4-butadiene) and may vary, for example, from between 45 and 65° C., (d) ABA triblock copolymers having a central poly(tetrahydrofuran) block (B block) with number-average molecular weight between 4100 and 18800 and having terminal poly(2-methyl-2-oxazoline) blocks (A blocks) with molecular weights of 1500, for which the A blocks exhibit glass transition temperatures around 80° C. and represent the hard phase segment, and for which the thermally induced shape memory effect is triggered by the melting temperature of the B blocks and may vary, for example, between 20 and 40° C., and (e) biodegradable block copolymers having at least one hard phase segment such as poly(p-dioxanone) and at least one amorphous switching phase segment such as $\epsilon$-caprolactone ($T_m$=46-64° C.).

Specific examples of multiblock copolymers with $T_{trans}=T_g$ include (a) polyurethanes with polyether switching phase segments, for example, polyetherurethanes such as those with a hard phase segment formed from methylenebis (4-phenylisocyanate) (MDI) and 1,4-butanediol, and a switching phase segment formed from tetrahydrofuran ($M_n$=250-2900), for which the thermally induced shape memory effect may vary, for example, from −56 to 54° C., (b) polyurethanes with polyester switching phase segments, for example, polyesterurethanes such as those with a hard phase segments synthesized from MDI and 1,4-butanediol and a switching phase segment formed from poly(ethylene adipate), for which the glass transition temperatures obtained with switching segments having weight average molecular weights of 300, 600, and 1000 at a constant hard segment content of 75 mol % decreases from 48 to −5° C. with increasing molecular weight of the poly(ethylene adipate) segments, and for which glass transition temperatures obtained with a switching phase segment with a weight average molecular weight of 600 increases from 13 to 35° C. as the hard-segment content increases from 75 to 90 mol %, (c) a series of block copolymers described in U.S. Pat. No. 5,128,197 to Mitsubishi Heavy Industries, which may have glass transition temperatures in the range of form −45 to 48° C., and (d) biodegradable block copolymers having at least one hard segment such as poly(p-dioxanone) and at least one amorphous switching segment such as poly(l-lactide)-co-glycolide ($T_g$=35-50° C.).

Other examples of shape memory polymers include polynorbornene such as NORSOREX, a linear, amorphous polynorbornene developed by CdF Chemie/Nippon, having a molecular weight of about three million, having about 70 to 80 mol % of trans-linked norbornene units, and having a glass transition temperature between 35 and 45° C. (the material softens abruptly above the glass transition temperature Tg, and if the chains are stretched quickly in this state, and the material is rapidly cooled down again, it is possible to freeze the induced elastic stress within the material).

Unlike the physical crosslinks for the above copolymers, the permanent shape of shape memory polymer networks are stabilized via covalent crosslinks. Besides the crosslinks, such networks also generally contain flexible components in the form of amorphous chains. If the working temperature is above the $T_{trans}$ for these chains, the networks will be elastic. As with shape memory block copolymers, the $T_{trans}$ thermal transition chosen for the fixation of the temporary shape may be a melting point or a glass transition temperature. After deforming the material at a temperature above the $T_{trans}$, the temporary deformed shape can be fixed by cooling the polymer below $T_{trans}$. Subsequent heating of the material above $T_{trans}$ returns the material to its permanent shape.

Certain hydrogels, such as hydrogels formed from copolymerized acrylic acid and stearyl acrylate, cross-linked with methylenebisacrylamide, are known to show a strong shape memory effect. Below about 25° C. these polymers behave like tough polymers, while above about 50° C. softening enables the materials to be stretched significantly by a deformation force. The stretched shape can be maintained by continuing to apply the deformation force during the cooling process. When the material is heated up again above the transition temperature the one-way shape memory effect takes place and the external shape in which the material was produced initially is recovered. The permanent shape is predetermined by the covalent polymer network.

Further information on shape memory polymers, such as shape memory gels, block copolymers and covalently cross-linked shape polymer networks can be found, for example, in A. Lendlein and S. Kelch, "Shape Memory Polymers" *Angew. Chem. Int. Id.* 2002, 41, 2034-2057 and the references cited therein.

U.S. Patent Application No. 2003/0055198 to Langer et al. also describes a wide range of shape memory polymer compositions, which include a hard segment and at least one soft segment, and which can hold more than one shape in memory, if desired. At least one of the hard or soft segments can contain a crosslinkable group, and the segments can be linked by formation of an interpenetrating network or a semi-interpenetrating network, or by physical interactions of the blocks. As above, the polymer can return to its original shape by heating the object above the $T_{trans}$ of the soft segment and below the $T_{trans}$ of the hard segment. The compositions can also include two soft segments which are linked via functional groups that are cleaved in response to application of light, electric field, magnetic field or ultrasound. The cleavage of these groups causes the object to return to its original shape. The hard and soft segments can be selected, for example, from polyhydroxy acids, polyorthoesters, polyether esters such as oligo (p-dioxanone), polyesters, polyamides, polyesteramides, polydepsidpetides, aliphatic polyurethanes, polysaccharides, polyhydroxyalkanoates, and copolymers thereof.

Shape memory polymers that utilize light for as an activation stimulus are known. For example, A. Lendlein et al., *Nature*, Vol. 434, 14 Apr. 2005, 879-882, report polymers containing cinnamic groups which can be deformed and fixed into a temporary shape by exposure to ultraviolet light illumination of a first wavelength (i.e., $\lambda > 260$ nm). The polymers can subsequently recover their original shape at upon exposure to ultraviolet light of a different wavelength (i.e., $\lambda < 260$ nm). Two photoresponsive shape-memory polymers are created in Lendlein et al., one in which cinnamic acid (CA) molecules are grafted onto a permanent polymer network (i.e., n-butylacrylate (BA), hydroxyethyl methacrylate (HEMA) and ethyleneglycol-1-acrylate-2-CA (HEA-CA), are copolymerized and crosslinked with poly(propylene glycol)-dimethacrylate), and one in which cinnamylidene acetic acid (CAA) molecules are provided in an interpenetrating network polymer (i.e., a permanent network is formed from poly(n-butyl acrylate) using poly(propylene glycol)-dimethacrylate as a crosslinker, and loaded with star-poly (ethylene glycol) containing CAA terminal groups). See also U.S. Pat. No. 2003/0055198 to R. S. Langer and A. Lendlein.

In some embodiments, drug delivery members in accordance with the present invention may be employed as matrices for drug storage and release or they may be provided with one or more drug-containing regions (e.g., layers, depressions, slits, etc.) for drug storage and release. Drug delivery members in accordance with the present invention may be provided with one or more drug delivering structures. For example, tubular members in accordance with the may be provided with small holes, allowing a drug-containing fluid to be delivered from the delivery members.

In certain embodiments, the drug-containing regions and the drug-containing fluids either consist essentially of the drug or include the drug and an additional material.

One example of such an additional material is iopromide (an iodine-based contrast medium) which is known to significantly increase the solubility of antirestenotic drugs in saline (specifically, paclitaxel). Iopromide is also known to adhere to vessel walls for several seconds after exposure and thus may act as a temporary in vivo matrix for antirestenotic drugs such as paclitaxel. See, e.g., B. Scheller et al., *Journal of the American College of Cardiology*, 42(8), 2003, 1415-1420.

Other examples of such additional materials include water soluble materials such as sugars, etc. Depending on the dissolution rate of the additional material, such embodiments may be most useful where the drug delivery member is inserted into the body while disposed in a tubular member (e.g., within an elongated tube from which the drug delivery member emerges, within a protective sheath which is pulled back from the drug delivery member, etc.).

Other examples of such additional materials include polymers.

In certain embodiments, the drug delivery members may be provided with tissue penetrating elements such as cutting blades or needles/spikes. These tissue penetrating elements may be further provided with a soft material covering (e.g., a soft polymer, which may further comprise one or more drugs) from which the tissue penetrating elements protrude upon radial expansion of the drug delivery members.

Drug delivery in certain embodiments, may also be assisted by heating the drug-containing regions, for example, by the passage of electrical current through the drug-containing regions and/or drug delivery members, by the passage of heated fluid through the drug delivery members (e.g., where tubular drug delivery members are employed), and by shining light on the drug-containing regions. Where the drug delivery members comprise a shape memory material, the heat that is used to expand the members can also be used to enhance drug delivery.

In this regard, as a general rule, the diffusion rate of a drug from a given material increases with increasing temperature. Moreover, in certain embodiments, temperature sensitive carrier materials may be employed for drug delivery. Such carrier materials may correspond, for instance, to the drug delivery member itself (e.g., where the drug delivery member acts as a drug-releasing matrix), to drug-containing compositions disposed on or within depressions in the drug delivery members, and so forth.

For example, temperature-sensitive hydrogels are known, which are able to swell or shrink in aqueous fluids as a result of a change in temperature of the surrounding fluid. Negative temperature-sensitive hydrogels have a lower critical solution temperature (LCST). They contract when heated above the LCST and expand when cooled below the LCST. Examples of hydrogels having an LCST include N-isopropylacryamide (NIPAAm) homopolymers and copolymers. Positive temperature-sensitive hydrogels have an upper critical solution temperature (UCST). They contract when cooled below the UCST and expand when heated above the UCST. Examples of hydrogels having a UCST include polymer networks of poly(acrylic acid) (PAA) and polyacrylamide (PAAm) homopolymers or copolymers such as poly(acrylamide-co-butyl methacrylate), among many others.

In the present invention, such materials may be selected, for example, wherein the LCST or UCST of the hydrogel is somewhat greater than normal body temperature (e.g., ranging from 38 to 40 to 42 to 44 to 46 to 48 to 50° C. or more). For example, by providing a drug delivery member in accordance with the invention with a coating of a drug-containing hydrogel with an LCST in this range, the coating can be contracted by heating above the LCST (and expanded by cooling/allowing to cool below the LCST). Analogously, by providing a drug delivery member in accordance with the invention with a coating of a drug-containing hydrogel with an UCST in this range, the coating can be expanded by heating above the UCST (and contracted by cooling/allowing to cool below the LCST). In either case, the materials may be passed through multiple expanded/contracted states by cycling the temperature through the LCST/UCST.

In other embodiments, temperature sensitive liposomes are included within the devices of the invention (e.g., within a drug delivery member, within a drug-containing composition disposed on or within depressions in a drug delivery member, etc.), which liposomes contain a therapeutic agent whose release increases dramatically with an increase in temperature above a given transition temperature. Specific examples of such lioposomes include DPPC-containing thermosensitive liposomes (where DPPC is 2-di-palmitoyl-sn-glycero-3-phosphocholine) such as those described in D. Needham et al., *Advanced Drug Delivery Reviews*, 53 (2001) 285-305. For instance, a drug delivery member in accordance with the invention may be provided with a thermosensitive-liposome-containing coating, in which case drug delivery can be enhanced by heating the coating above the transition temperature of the liposomes.

"Therapeutic agents", "pharmaceuticals," "pharmaceutically active agents", "drugs" and other related terms may be used interchangeably herein and include genetic therapeutic agents, non-genetic therapeutic agents and cells. Therapeutic agents may be used singly or in combination. Therapeutic agents may be, for example, nonionic or they may be anionic and/or cationic in nature. A wide variety of therapeutic agents can be employed in conjunction with the present invention including those used for the treatment of a wide variety of diseases and conditions (i.e., the prevention of a disease or condition, the reduction or elimination of symptoms associated with a disease or condition, or the substantial or complete elimination of a disease or condition).

Exemplary non-genetic therapeutic agents for use in connection with the present invention include: (a) anti-thrombotic agents such as heparin, heparin derivatives, urokinase, clopidogrel, and PPack (dextrophenylalanine proline arginine chloromethylketone); (b) anti-inflammatory agents such as dexamethasone, prednisolone, corticosterone, budesonide, estrogen, sulfasalazine and mesalamine; (c) antineoplastic/antiproliferative/anti-miotic agents such as paclitaxel, 5-fluorouracil, cisplatin, vinblastine, vincristine, epothilones, endostatin, angiostatin, angiopeptin, monoclonal antibodies capable of blocking smooth muscle cell proliferation, and thymidine kinase inhibitors; (d) anesthetic agents such as lidocaine, bupivacaine and ropivacaine; (e) anti-coagulants such as D-Phe-Pro-Arg chloromethyl ketone, an RGD peptide-containing compound, heparin, hirudin, antithrombin compounds, platelet receptor antagonists, anti-thrombin antibodies, anti-platelet receptor antibodies, aspirin, prostaglandin inhibitors, platelet inhibitors and tick antiplatelet peptides; (f) vascular cell growth promoters such as growth factors, transcriptional activators, and translational promotors; (g) vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; (h) protein kinase and tyrosine kinase inhibitors (e.g., tyrphostins, genistein, quinoxalines); (i) prostacyclin analogs; (j) cholesterol-lowering agents; (k) angiopoietins; (l) antimicrobial agents such as triclosan, cephalosporins, aminoglycosides and nitrofurantoin; (m) cytotoxic agents, cytostatic agents and cell proliferation affectors; (n) vasodilating agents; (o) agents that interfere with endogenous vasoactive mechanisms; (p) inhibitors of leukocyte recruitment, such as monoclonal antibodies; (q) cytokines; (r) hormones; (s) inhibitors of HSP 90 protein (i.e., Heat Shock Protein, which is a molecular chaperone or housekeeping protein and is needed for the stability and function of other client proteins/signal transduction proteins responsible for growth and survival of cells) including geldanamycin, (t) smooth muscle relaxants such as alpha receptor antagonists (e.g., doxazosin, tamsulosin, terazosin, prazosin and alfuzosin), calcium channel blockers (e.g., verapimil, diltiazem, nifedipine, nicardipine, nimodipine and bepridil), beta receptor agonists (e.g., dobutamine and salmeterol), beta receptor antagonists (e.g., atenolol, metaprolol and butoxamine), angiotensin-II receptor antagonists (e.g., losartan, valsartan, irbesartan, candesartan, eprosartan and telmisartan), and antispasmodic/anticholinergic drugs (e.g., oxybutynin chloride, flavoxate, tolterodine, hyoscyamine sulfate, diclomine), (u) bARKct inhibitors, (v) phospholamban inhibitors, (w) Serca 2 gene/protein, (x) immune response modifiers including aminoquizolines, for instance, imidazoquinolines such as resiquimod and imiquimod, (y) human apolioproteins (e.g., AI, AII, AIII, AIV, AV, etc.), (z) selective estrogen receptor modulators (SERMs) such as raloxifene, lasofoxifene, arzoxifene, miproxifene, ospemifene, PKS 3741, MF 101 and SR 16234, (aa) PPAR agonists, including PPAR-alpha, gamma and delta agonists, such as rosiglitazone, pioglitazone, netoglitazone, fenofibrate, bexaotene, metaglidasen, rivoglitazone and tesaglitazar, (bb) prostaglandin E agonists, including PGE2 agonists, such as alprostadil or ONO 8815Ly, (cc) thrombin receptor activating peptide (TRAP), (dd) vasopeptidase inhibitors including benazepril, fosinopril, lisinopril, quinapril, ramipril, imidapril, delapril, moexipril and spirapril, (ee) thymosin beta 4, (ff) phospholipids including phosphorylcholine, phosphatidylinositol and phosphatidylcholine, (gg) VLA-4 antagonists and VCAM-1 antagonists.

Preferred non-genetic therapeutic agents include taxanes such as paclitaxel (including particulate forms thereof, for instance, protein-bound paclitaxel particles such as albumin-bound paclitaxel nanoparticles, e.g., ABRAXANE), sirolimus, everolimus, tacrolimus, zotarolimus, biolimus, Epo D, dexamethasone, estradiol, halofuginone, cilostazole, geldanamycin, alagebrium chloride (ALT-711), ABT-578 (Abbott Laboratories), trapidil, liprostin, Actinomcin D, Resten-NG, Ap-17, abciximab, clopidogrel, Ridogrel, beta-blockers, bARKct inhibitors, phospholamban inhibitors, Serca 2 gene/protein, imiquimod, human apolioproteins (e.g., AI-AV), growth factors (e.g., VEGF-2), as well derivatives of the forgoing, among others.

Numerous therapeutic agents, not necessarily exclusive of those listed above, have been identified as candidates for vascular treatment regimens, for example, as agents targeting restenosis (antirestenotics). Such agents are useful for the practice of the present invention and include one or more of the following: (a) Ca-channel blockers including benzothiazapines such as diltiazem and clentiazem, dihydropyridines such as nifedipine, amlodipine and nicardapine, and phenylalkylamines such as verapamil, (b) serotonin pathway modulators including: 5-HT antagonists such as ketanserin and naftidrofuryl, as well as 5-HT uptake inhibitors such as fluoxetine, (c) cyclic nucleotide pathway agents including phosphodiesterase inhibitors such as cilostazole and dipyridamole, adenylate/Guanylate cyclase stimulants such as forskolin, as well as adenosine analogs, (d) catecholamine modulators including α-antagonists such as prazosin and bunazosine, β-antagonists such as propranolol and α/β-antagonists such as labetalol and carvedilol, (e) endothelin receptor antagonists such as bosentan, sitaxsentan sodium, atrasentan, endonentan, (f) nitric oxide donors/releasing molecules including organic nitrates/nitrites such as nitroglycerin, isosorbide dinitrate and amyl nitrite, inorganic nitroso compounds such as sodium nitroprusside, sydnonimines such as molsidomine and linsidomine, nonoates such as diazenium diolates and NO adducts of alkanediamines, S-nitroso compounds including low molecular weight compounds (e.g., S-nitroso derivatives of captopril, glutathione and N-acetyl penicillamine) and high molecular weight compounds (e.g., S-nitroso derivatives of proteins, peptides, oligosaccharides, polysaccharides, synthetic polymers/oligomers and natural polymers/oligomers), as well as C-nitroso-compounds, O-nitroso-compounds, N-nitroso-compounds and L-arginine, (g) Angiotensin Converting Enzyme (ACE) inhibitors such as cilazapril, fosinopril and enalapril, (h) ATII-receptor antagonists such as saralasin and losartin, (i) platelet adhesion inhibitors such as albumin and polyethylene oxide, (j) platelet aggregation inhibitors including cilostazole, aspirin and thienopyridine (ticlopidine, clopidogrel) and GP IIb/IIIa inhibitors such as abciximab, epitifibatide and tirofiban, (k) coagulation pathway modulators including heparinoids such as heparin, low molecular weight heparin, dextran sulfate and β-cyclodextrin tetradecasulfate, thrombin inhibitors such as hirudin, hirulog, PPACK(D-phe-L-propyl-L-arg-chloromethylketone) and argatroban, FXa inhibitors such as antistatin and TAP (tick anticoagulant peptide), Vitamin K inhibitors such as warfarin, as well as activated protein C, (l) cyclooxygenase pathway inhibitors such as aspirin, ibuprofen, flurbiprofen, indomethacin and sulfinpyrazone, (m) natural and synthetic corticosteroids such as dexamethasone, prednisolone, methprednisolone and hydrocortisone, (n) lipoxygenase pathway inhibitors such as nordihydroguairetic acid and caffeic acid, (o) leukotriene receptor antagonists, (p) antagonists of E- and P-selectins, (q) inhibitors of VCAM-1 and ICAM-1 interactions, (r) prostaglandins and analogs thereof including prostaglandins such as PGE1 and PGI2 and prostacyclin analogs such as ciprostene, epoprostenol, carbacyclin, iloprost and beraprost, (s) macrophage activation preventers including bisphosphonates, (t) HMG-CoA reductase inhibitors such as lovastatin, pravastatin, atorvastatin, fluvastatin, simvastatin and cerivastatin, (u) fish oils and omega-3-fatty acids, (v) free-radical scavengers/antioxidants such as probucol, vitamins C and E, ebselen, trans-retinoic acid, SOD (orgotein) and SOD mimics, verteporfin, rostaporfin, AGI 1067, and M 40419, (w) agents affecting various growth factors including FGF pathway agents such as bFGF antibodies and chimeric fusion proteins, PDGF receptor antagonists such as trapidil, IGF pathway agents including somatostatin analogs such as angiopeptin and ocreotide, TGF-β pathway agents such as polyanionic agents (heparin, fucoidin), decorin, and TGF-β antibodies, EGF pathway agents such as EGF antibodies, receptor antagonists and chimeric fusion proteins, TNF-α pathway agents such as thalidomide and analogs thereof, Thromboxane A2 (TXA2) pathway modulators such as sulotroban, vapiprost, dazoxiben and ridogrel, as well as protein tyrosine kinase inhibitors such as tyrphostin, genistein and quinoxaline derivatives, (x) matrix metalloprotease (MMP) pathway inhibitors such as marimastat, ilomastat, metastat, batimastat, pentosan polysulfate, rebimastat, incyclinide, apratastat, PG 116800, RO 1130830 or ABT 518, (y) cell motility inhibitors such as cytochalasin B, (z) antiproliferative/antineoplastic agents including antimetabolites such as purine antagonists/analogs (e.g., 6-mercaptopurine and pro-drugs of 6-mercaptopurine such as azathioprine or cladribine, which is a chlorinated purine nucleoside analog), pyrimidine analogs (e.g., cytarabine and 5-fluorouracil) and methotrexate, nitrogen mustards, alkyl sulfonates, ethylenimines, antibiotics (e.g., daunorubicin, doxorubicin), nitrosoureas, cisplatin, agents affecting microtubule dynamics (e.g., vinblastine, vincristine, colchicine, Epo D, paclitaxel and epothilone), caspase activators, proteasome inhibitors, angiogenesis inhibitors (e.g., endostatin, angiostatin and squalamine), olimus family drugs (e.g., sirolimus, everolimus, tacrolimus, zotarolimus, etc.), cerivastatin, flavopiridol and suramin, (aa) matrix deposition/organization pathway inhibitors such as halofuginone or other quinazolinone derivatives, pirfenidone and tranilast, (bb) endothelialization facilitators such as VEGF and RGD peptide, (cc) blood rheology modulators such as pentoxifylline and (dd) glucose cross-link breakers such as alagebrium chloride (ALT-711).

Numerous additional therapeutic agents useful for the practice of the present invention are also disclosed in U.S. Pat. No. 5,733,925 to Kunz.

Although various embodiments are specifically illustrated and described herein, it will be appreciated that modifications and variations of the present invention are covered by the above teachings and are within the purview of the appended claims without departing from the spirit and intended scope of the invention.

The invention claimed is:

1. A drug delivery device comprising an elongated tubular member, an elongated actuation member and a curved elongated non-balloon drug delivery member that is adapted for expansion in a body lumen for drug delivery, followed by contraction and removal from the body lumen, said curved elongated drug delivery member progressing from a radially compressed configuration to a radially expanded configuration upon actuation in vivo, wherein said curved elongated drug delivery member is in the form of a helix, wherein said helix decreases in stiffness as one proceeds from its proximal end to its distal end, wherein said drug delivery member is attached at or near its proximal end to a position at or near a distal end of said elongated tubular member, wherein said elongated actuation member is attached at or near its distal end to a position at or near a distal end of said drug delivery member, and wherein said drug delivery member is placed in a radially expanded configuration by distally advancing the elongated tubular member, by proximally retracting the elongated actuation member, or a combination of both.

2. A drug delivery device comprising an elongated tubular member, an elongated actuation member and a curved elongated non-balloon drug delivery member that is adapted for expansion in a body lumen for drug delivery, followed by contraction and removal from the body lumen, said curved elongated drug delivery member progressing from a radially compressed configuration to a radially expanded configuration upon actuation in vivo, wherein said curved elongated drug delivery member is in the form of a helix, wherein said helix decreases in stiffness as one proceeds from its proximal end to its distal end, wherein said drug delivery member is attached at or near its proximal end to a position at or near a distal end of said elongated tubular member, wherein said elongated actuation member is attached at or near its distal end to a position at or near a distal end of said drug delivery member, and wherein said drug delivery member is placed in a radially expanded configuration by rotating the elongated tubular member relative to the elongated actuation member.

3. A drug delivery device comprising (a) a curved elongated non-balloon drug delivery member that is adapted for expansion in a body lumen for drug delivery, followed by contraction and removal from the body lumen, said curved elongated drug delivery member progressing from a radially compressed configuration to a radially expanded configuration upon actuation in vivo, wherein said curved elongated drug delivery member is in the form of a helix, and wherein said helix decreases in stiffness as one proceeds from its proximal end to its distal end and (b) a flexible drug-containing sheath over said drug delivery member such that said drug-containing sheath is radially expanded by the underlying drug delivery member.

4. A drug-delivery device comprising a soft polymeric non-balloon drug delivery member that comprises a plurality of wings, an elongated tubular member, and an elongated actuation member which is (a) is adapted to advance said drug delivery member from said elongated tubular member such that said drug delivery member elastically rebounds and adopts a radially expanded configuration, wherein a plurality of channels are formed between a vessel wall and the drug delivery member upon radial expansion in said vessel and (b) is adapted to withdraw said drug delivery member into said elongated tubular member such that said drug delivery member returns to a radially compressed configuration.

5. The drug-delivery device of claim 4, wherein said drug delivery member is attached at or near its proximal end to a position at or near a distal end of said elongated actuation member.

6. A drug delivery device comprising (a) an elongated non-balloon drug delivery member that is adapted for expansion in a body lumen for drug delivery, followed by contraction and removal from the body lumen, said curved elongated drug delivery member progressing from a radially compressed configuration to a radially expanded configuration upon actuation in vivo, (b) an elongated actuation member, said elongated actuation member being slidably disposed within an off-center lumen within said elongated drug delivery member and said elongated actuation member being attached to a distal end of said elongated drug delivery member, wherein said drug delivery member forms a helix when said elongated actuation member is pulled relative to the drug delivery member and (c) an additional off-center lumen containing a wire that is fixed along its length to the elongated drug delivery member.

7. The drug delivery device of claim 6, wherein said wire forms a helix that differs in shape from the helix formed by the drug delivery member.

8. A drug delivery device comprising (a) an elongated non-balloon drug delivery member that is adapted for expansion in a body lumen for drug delivery, followed by contraction and removal from the body lumen, said curved elongated drug delivery member progressing from a radially compressed configuration to a radially expanded configuration upon actuation in vivo, (b) an elongated actuation member, said elongated actuation member being slidably disposed within an off-center lumen within said elongated drug delivery member and said elongated actuation member being attached to a distal end of said elongated drug delivery member, wherein said drug delivery member forms a helix when said elongated actuation member is pulled relative to the drug delivery member and wherein the elongated drug delivery member comprises a plurality of slits that contain said drug, and wherein said slits face a wall of said body lumen upon formation of said helix.

9. The drug-delivery device of claim, 4, wherein said drug delivery member has a star-shaped cross-section.

10. The drug-delivery device of claim 9, wherein the cross sectional shape rotates as one advances along the axis of the device.

11. The drug-delivery device of claim 4, wherein said wings preferentially fold in a clockwise or counterclockwise direction when returned to a radially compressed configuration.

12. The drug-delivery device of claim 4, wherein a proximal end of the drug delivery member is tapered to assist refolding when the drug delivery member is withdrawn into the elongated tubular member.

13. The drug-delivery device of claim 4, comprising three or more wings.

14. The drug-delivery device of claim 4, comprising four or more wings.

15. The drug-delivery device of claim 4, wherein a drug depot is formed at the end of each wing.

16. The drug-delivery device of claim 4, wherein drug is loaded into depressions in said wings.

17. The drug-delivery device of claim 4, wherein said device is configured to inject a drug-containing fluid into said channels.

18. The drug-delivery device of claim 4, further comprising a catheter with a balloon which is configured to be inserted into one of said channels and which is configured to close off a distal end of the channel by inflating the balloon.

* * * * *